United States Patent [19]

Noguchi et al.

[11] Patent Number: 4,863,691
[45] Date of Patent: Sep. 5, 1989

[54] GAS-PASSAGE CHANGE-OVER APPARATUS

[76] Inventors: Naoki Noguchi; Yo Fukui, both of c/o Horbia, Ltd., 2 Miyanohigashi-machi, Kissyoin, Minami-ku, Kyoto, Japan

[21] Appl. No.: 135,506

[22] Filed: Dec. 18, 1987

Related U.S. Application Data

[63] Continuation of Ser. No. 910,272, Sep. 17, 1986, abandoned, which is a continuation of Ser. No. 671,762, Nov. 14, 1984, abandoned.

[30] Foreign Application Priority Data

Dec. 3, 1983 [JP] Japan ................................ 58-187362

[51] Int. Cl.$^4$ ...................... G01N 31/00; G01N 21/00
[52] U.S. Cl. ......................................... 422/54; 73/23; 422/52; 422/93; 436/158; 436/172
[58] Field of Search ................. 422/52, 54, 93, 94, 422/83; 436/158, 172, 118, 116, 141; 73/23

[56] References Cited

U.S. PATENT DOCUMENTS

| | | | |
|---|---|---|---|
| 3,224,838 | 12/1965 | Evans | 422/93 |
| 3,667,914 | 6/1972 | Penguite | 422/93 |
| 3,765,247 | 10/1973 | Riggs | 422/93 |
| 3,963,928 | 6/1976 | Zolner | 422/52 |
| 4,520,651 | 6/1985 | Litman | 73/23 |
| 4,555,931 | 12/1985 | Amimoto | 73/23 |

Primary Examiner—Kenneth M. Schor

[57] ABSTRACT

A gas-passage change-over apparatus, in which two gas lines are connected to one detector so that either of the two gas lines may be opened into the detector under the condition that the pressures at the ends of the two gas lines having different volumes are regulated by a pressure regulator. Switching valves are provided in each of the gas lines, and the connection of the flow from the gas lines to the detector is changed over by means of the two switching valves, such that switching valves are both closed for a predetermined period of time between changeovers.

6 Claims, 3 Drawing Sheets the NO$_x$-line 2 to the NO-line 3 is different from the cases where the path of a sample is changed over from the NO-line 3 to the NO$_x$-line 2. It was found from the measurement that the difference in regulating pressure reached about 2%. Such a difference in regulating pressure directly leads to an error of measurement. In addition, it leads to a serious problem in cases, where the efficiency of a converter is checked. Furthermore, referring to FIG. 1, element 5 designates a line for feeding the detector 4 with O$_3$, and element 6 designates an ozonator, and element C$_{ap}$ designating a capillary.

GAS-PASSAGE CHANGE-OVER APPARATUS

This application is a continuation of now abandoned application Ser. No. 910,272 filed on Sept. 17, 1986 which in turn is a continuation of now abandoned application Ser. No. 671,762 filed on Nov. 14, 1984.

BACKGROUND OF THE INVENTION

Field of the Invention

The present invention relates to a gas-passage change-over apparatus in which two gas lines are connected to one detector through a switching valve so that either of said two gas lines may be opened into said detector under the condition that the pressures at the ends of said two gas lines having different volumes are regulated by means of a pressure regulator.

Description of the Prior Art

The apparatus of the type described above has been used in a forced chemical luminescence type NO$_x$-meter. The application to this NO$_x$-meter is shown in FIG. 1. Referring now to FIG. 1, F designates a filter; P designates a sampling suction pump, and V designates a three-way electro-magnetic valve. A sample, for example, air, drawn in by means of the sampling suction pump P, is passed through a NO$_x$-line 2, in which a converter 1 (an apparatus which changes NO$_2$ into NO, concretely speaking, a cylindrical member housing reducers therein) is provided, and also passed through a NO (nitrogen monoxide)-line 3 without the converter; the lines are changed over by means of the electro-magnetic valve V, and the combined output of the lines 2 and 3 are then transferred to the detector 4 where the concentration of NO is determined. In cases where a sample is transferred to the detector 4 through the NO$_x$-line 2, since not only NO contained in the sample but also NO obtained by the reduction of NO$_2$, produce outputs, the concentration of NO$_x$(=NO+NO$_2$) can be determined while, in cases where said sample is transferred to the detector 4 through the NO-line 3, only NO contained in the sample produces an output, whereby the concentration of NO contained in the sample can be determined.

By the way, in analyzers such as a NO$_x$-meter, the flow rate of a sample passing through the detector 4 must be controlled so as to be constant. To this end, also in such conventional apparatus the pressures at the ends A of the NO$_x$-line 2 and the NO-line 3 are controlled by means of a pressure regulator Reg. However, since the NO$_x$-line 2 is different from the NO-line 3 in volume, there is a problem that the pressures can not always be controlled so as to be constant. That is to say, since a converter is provided in the NO$_x$-line 2, the volume of the NO$_x$-line 2 is larger than that of the NO-line 3, so, in cases where the path of a sample is changed over from the NO$_x$-line 2 to the NO-line 3, the converter 1 acts as a buffer, whereby the pressure of a pressure regulating portion (the end of line) is temporarily raised while, in cases where the path of the sample is changed over from the NO-line 3 to the NO$_x$-line 2, contrary to that described above, the pressure of the pressure regulating portion is apt to be temporarily reduced. In general, since the regulating pressure of a pressure regulator in cases where the pressure is regulated from a lower pressure to a higher pressure is slightly different from that in cases where the pressure is regulated from a higher pressure to a lower pressure, the regulating pressure in the cases where the path of a sample is changed

SUMMARY OF THE INVENTION

In view of the above, it is an object of the present invention to provide a novel means, in which even though two gas lines are different in volume, the regulating pressure can be regulated so as to be always constant so that the pressure regulation may be always carried out from a lower pressure to a higher pressure in both manners of changing over lines, whereby the above described problems such as an error of measurement can be eliminated.

In order to achieve the above described object, the point of the present invention is that both gas lines are connected to one detector through switching valves so that either of the two gas lines may be opened into the detector under the condition that the pressures at the ends of the two gas lines having different volumes are regulated by means of a pressure regulator, the switching valves being provided in each of the two gas lines, and the connection of the gas lines with the detector being changed over by means of the switching valves, wherein both of the switching valves are closed for a predetermined period of time.

According to the present invention, since a switching valve is provided in each of two gas lines and the connection of the two gas lines with a detector is changed over by means of the switching valves, when both of the switching valves are closed for a predetermined period of time, the pressure regulation can be always carried out by raising the pressure whereby the regulating pressure of a pressure regulator can be made constant in both manners of changing over lines and as a result, an error of measurement resulting from the difference in regulating pressure can be eliminated, and in addition, the efficiency of a converter can be successfully checked.

DESCRIPTION OF THE PREFERRED EMBODIMENT

Figure 1:
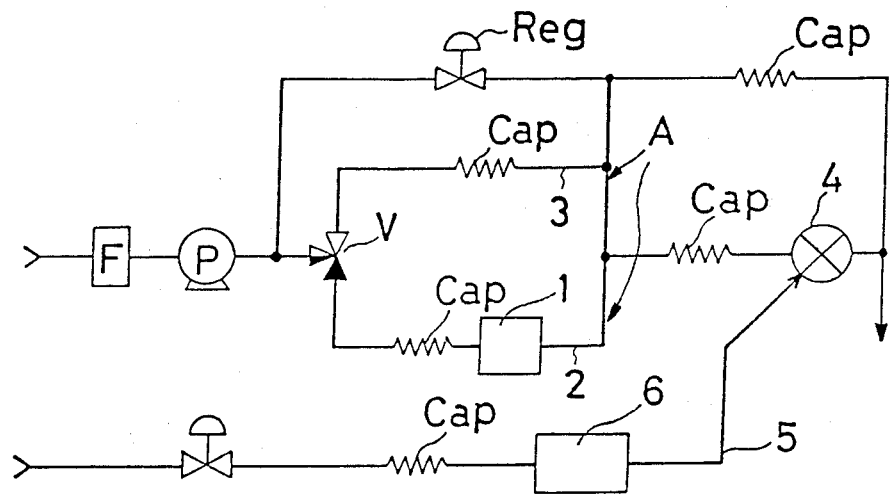
FIG. 1 is a diagram showing the conventional passage change-over apparatus.
Figure 2:
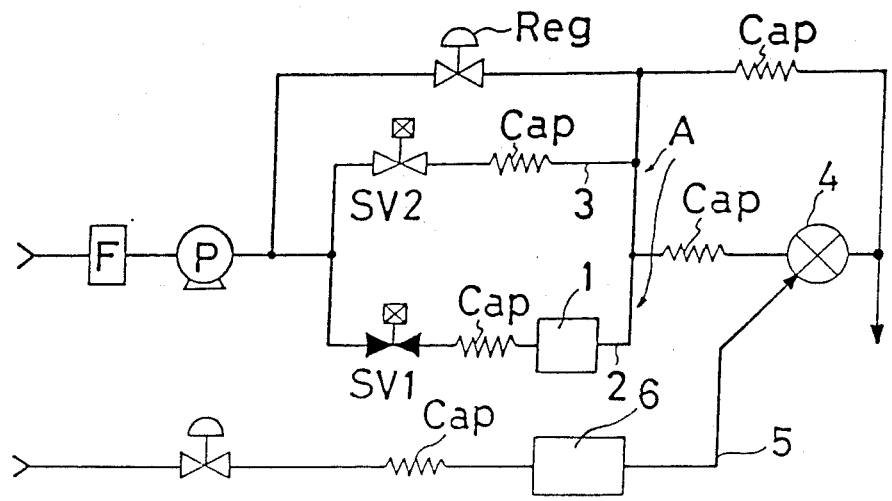
FIG. 2 is a diagram showing a preferred embodiment of a passage change-over apparatus according to the present invention.

FIG. 2 shows a passage change-over apparatus according to the present invention applied to a forced chemical luminescence type NO$_x$-meter. The same parts and elements as in a NO$_x$-meter shown in FIG. 1 are marked similarly to those in FIG. 1 and their explanation is omitted for the sake of brevity.

Figure 3:
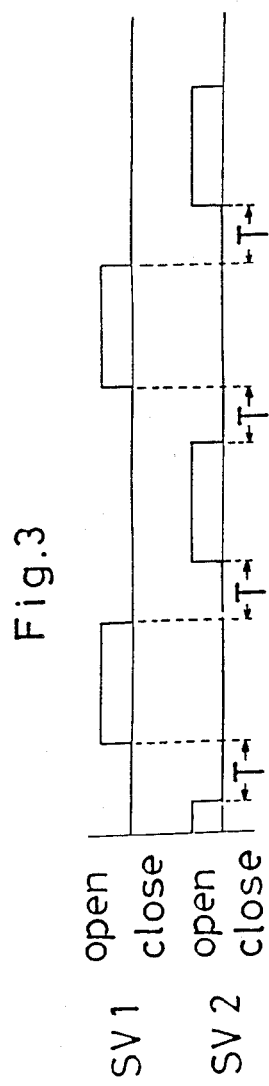
FIG. 3 is a time chart showing an on-off action of a switching valve.

The connection of a $NO_x$-line 2 and a NO-line 3 with a detector 4 is changed over by means of a switching valve $SV_1$ provided in the $NO_x$-line 2 and a switching valve $SV_2$ provided in the NO-line 3. Both switching valves $SV_1$ and $SV_2$ are closed for a predetermined period of time T (usually 1 to 2 seconds) during change-over of gas lines by controlling the electrification thereof in such a manner as shown in FIG. 3.

Thus, since a sample gas is not fed during the time when two switching valves are closed together, the pressure as the pressure regulating portion A (the ends of gas lines) is reduced and then it is regulated to the former pressure when either of the switching valves $SV_1$ and $SV_2$ is opened. That is to say, the pressure of the pressure regulating portion is regulated so as to be always constant in both manners of changing over gas lines since it is returned to the former pressure after being always once reduced. As a result, an error of measurement resulting from the difference in regulating pressure can be eliminated.

Figure 4:
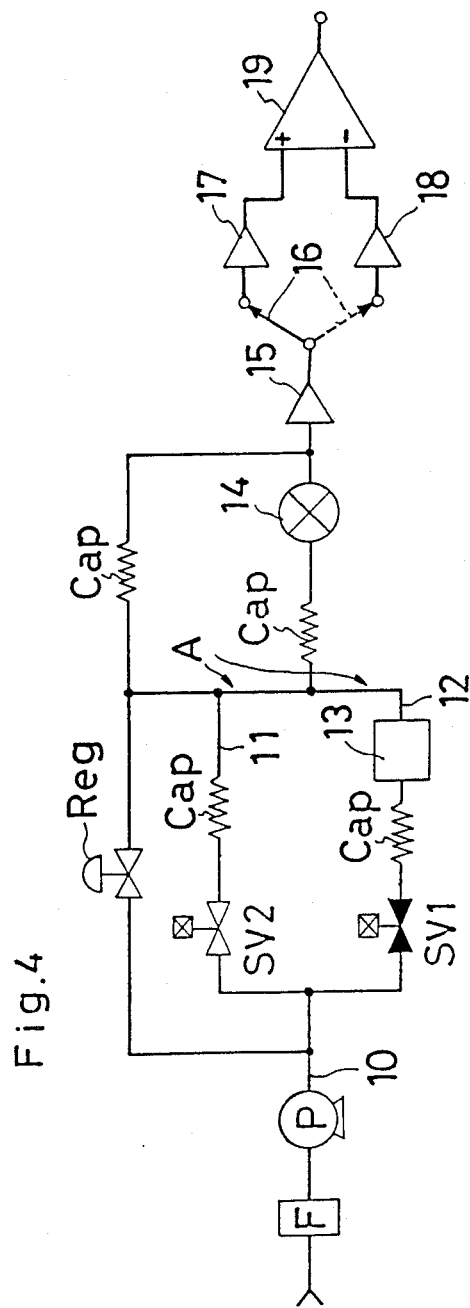
FIG. 4 is a block diagram showing another preferred embodiment of a passage change-over apparatus according to the present invention.

The present invention can be applied to every instrument, in which it is necessary to pass the constant flow rate of sample gas through a detector and two gas lines to be changed over to each other have different volumes, in addition to a $NO_x$-meter described in the above-described preferred embodiment. For example, it can be applied also to a hydrocarbon-meter as shown in FIG. 4 in which the total concentration of hydrocarbons contained in the sample and the concentration of methane contained in the sample are determined and then the concentration of non-methane hydrocarbons is determined by deducting the latter from the former. Furthermore, referring to FIG. 4, element 10 designates a sample gas line; element 11 designates a total hydrocarbon gas line; element 12 designates a methane gas line; element 13 designates a combustion tube (corresponding to the above described converter 1), in which hydrocarbon gases other than methane are burnt by utilizing the differences in combustion temperature, provided in the methane gas line 12 element; 14 designates a flame ionization detector element 15 designates a preamplifier element 16 designates a change-over switch which is changed over in conjunction with the on-off action of the switching valves $SV_1$ and $SV_2$; elements 17 and 18 designate holding amplifiers; element 19 designates a subtractor; the concentration of total hydrocarbons contained in the sample is determined when the sample is transferred to the detector 14 through the gas line 11, and the concentration of methane gas contained in the sample is determined when the sample is transferred to the detector 14 through the gas line 12, and the concentration of non-methane hydrocarbons is determined by subtracting the latter from the former.

We claim:

1. A gas-passage change-over apparatus comprising:
   a pressure regulator and two conduit means defining two gas lines, each having an inlet and an outlet, said two gas lines having different volumes from each other;
   each of said gas lines having a controllable valve located in the gas line between the inlet and outlet, each of said controllable valves being selectively controllable so as to be either open or closed;
   means connected to one of said gas lines for effecting a change in composition of a simple gas passing through the outlet of said one gas line compared to the composition of the sample gas passing through the outlet of the other one of the gas lines;
   another conduit means, said another conduit means defining a single feed line, connected to the inlets of both of said gas lines, for providing a fluid flow to both inlets;
   a detector connected to the outlets of both of said gas lines such that both of said gas lines are connected in parallel thereto and such that a fluid flow from each of said two gas lines is alternatively fed into said detector;
   said pressure regulator connected to the outlets of said two gas lines, said pressure regulator being a means for regulating the respective pressures at the outlets of said two gas lines such that said respective pressures are regulated by said pressure regulator so as to be equal to each other before and after a change-over of said gas passage through said gas lines to said detector so that a flow rate of a sample gas passing through said detector is constant;
   the volumes of the two gas lines differing to an extent such that a change-over in passage of fluid to the detector from one of the gas lines to the other of the gas lines causes a change in pressure at the outlets of the gas lines which in turn causes an error in measurement by the detector if the flow rate therethrough is not maintained constant;
   control means which automatically operates said controllable valves to control said controllable valves such that the fluid flow from said gas lines to said detector is changed over by said controllable valves and such that both of said controllable valves are simultaneously closed for a predetermined period of time during a change-over.

2. A gas-passage change-over apparatus as recited in claim 4, wherein said composition changing means is a converter means disposed downstream of one of said controllable valves in one of said two gas lines for changing $NO_2$ into NO, wherein said detector comprises a detecting means for detecting the concentration of NO, whereby said apparatus operates as an $NO_x$ meter.

3. A gas-passage change-over apparatus as recited in claim 4, wherein said composition changing means is a combustion tube means for burning hydrocarbon gases other than methane by using differences in combustion temperature disposed downstream of one of said controllable valves in one of said gas lines, wherein said detector comprises a flame ionization detector means whereby said apparatus operates as a hydrocarbon meter.

4. A gas-passage change-over apparatus comprising:
   a pressure regulator and two conduit means defining two gas lines, each having an inlet and an outlet, said two gas lines having different volumes from each other;
   each of said gas lines having a controllable valve located in the gas line between the inlet and outlet, each of said controllable valves being selectively controllable so as to be either open or closed;
   feed conduit means comprising a single feed line connected to the inlets of both of said gas lines for providing a fluid flow to both inlets;
   a detector connected to the outlets of both of said gas lines such that both of said gas lines are connected in parallel thereto and such that a fluid flow from each of said two gas lines is alternatively fed into said detector;

said pressure regulator being connected to the outlets of said two gas lines, said pressure regulator comprising a means for regulating the respective pressures at the outlets of said two gas lines such that said respective pressures are regulated by said pressure regulator so as to be equal to each other before and after a change-over of said gas passage through said gas lines to said detector so that a flow rate of a sample gas passing through said detector is constant;

the volumes of the two gas lines differing to an extent such that a change-over in passage of fluid to the detector from one of the gas lines to the other of the gas lines causes a change in pressure at the outlets of the gas lines which in turn causes an error in measurement by the detector if the flow rate therethrough is not maintained constant; and control means for automatically operating said controllable valves to control said controllable valves such that the fluid flow from said gas lines to said detector is changed over by said controllable valves and such that both of said controllable valves are simultaneously closed for a predetermined period of time during a change-over.

5. A gas-passage change-over apparatus as recitefd in claim 7, further comprising means located in one of said gas lines for effecting a change in composition of a sample gas passing through the outlet of said one gas line compared to the composition of the sample gas passing through the outlet of the other one of the gas lines, said composition changing means comprising a converter means disposed downstream of one of said controllable valves in one of said two gas lines for changing $NO_2$ into NO, whereby said apparatus operates as an $NO_x$ meter.

6. A gas-passage change-over apparatus as recited in claim 7, further comprising means located in one of said gas lines for effecting a change in composition of a sample gas passing through the outlet of said one gas line compared to the composition of the sample gas passing through the outlet of the other one of the gas lines, said composition changing means comprising a combustion tube means for burning hydrocarbon gases other then methane by using differences in combustion temperature disposed downstream of one of said controllable valves in one of said gas lines, whereby said apparatus operates as a hydrocarbon meter.

* * * * *